(12) United States Patent  
Miller et al.

(10) Patent No.: US 12,042,178 B2  
(45) Date of Patent: Jul. 23, 2024

(54) SYSTEM OF MEDICAL DEVICES AND METHOD FOR PERICARDIAL PUNCTURE

(71) Applicant: Boston Scientific Medical Device Limited, Ballybrit (IE)

(72) Inventors: Brock Miller, Toronto (CA); Matthew Gravett, Milton (CA); Kai-Lon Fok, Mississauga (CA); Rund Abou-Marie, Mississauga (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 209 days.

(21) Appl. No.: 17/377,714

(22) Filed: Jul. 16, 2021

(65) Prior Publication Data

US 2022/0022914 A1  Jan. 27, 2022

Related U.S. Application Data

(60) Provisional application No. 63/054,439, filed on Jul. 21, 2020.

(51) Int. Cl.
*A61B 17/34* (2006.01)
*A61B 1/313* (2006.01)
(Continued)

(52) U.S. Cl.
CPC .......... *A61B 17/3478* (2013.01); *A61B 1/313* (2013.01); *A61B 6/12* (2013.01);
(Continued)

(58) Field of Classification Search
CPC . A61B 1/00154; A61B 1/313; A61B 17/3403; A61B 17/3478; A61B 18/1402; A61B 18/1477; A61B 2017/00247; A61B 2018/00351; A61B 2018/00363; A61B 2018/00982; A61B 2018/1425; A61B 2090/3614; A61B 2090/376; A61B 2090/3966; A61B 6/12; A61B 6/485; A61B 90/361; A61B 90/37
See application file for complete search history.

(56) References Cited

U.S. PATENT DOCUMENTS

175,254 A  3/1876 Oberly
827,626 A  7/1906 Gillet
(Continued)

*Primary Examiner* — Mark D Remaly
(74) *Attorney, Agent, or Firm* — Nelson Mullins Riley & Scarborough LLP (57) ABSTRACT

A system of medical devices includes a needle, an endoscope, and an introducer. The needle extends between a needle proximal portion and a needle distal portion having a puncturing tip. The endoscope extends between an endoscope proximal portion and an endoscope distal portion having a camera. The introducer is for guiding the needle and the endoscope towards a target location. The introducer extends between an introducer proximal portion and an introducer distal portion and has a first lumen extending therethrough from the introducer proximal portion to the introducer distal portion and a second lumen extending therethrough from the introducer proximal portion to the introducer distal portion. The needle is advanceable through the first lumen to position the puncturing tip proud of the introducer distal portion and the endoscope is advanceable through the second lumen to position the camera proximate the introducer distal portion and outside of the lumen.

17 Claims, 4 Drawing Sheets

(51) Int. Cl.
*A61B 6/00* (2006.01)
*A61B 6/12* (2006.01)
*A61B 18/14* (2006.01)
*A61B 18/00* (2006.01)
*A61B 90/00* (2016.01)

(52) U.S. Cl.
CPC .......... *A61B 6/485* (2013.01); *A61B 17/3403* (2013.01); *A61B 18/1477* (2013.01); *A61B 2018/00363* (2013.01); *A61B 2090/3966* (2016.02)

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |

(56) References Cited

U.S. PATENT DOCUMENTS

| | | |
|---|---|---|
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |

(56) References Cited

U.S. PATENT DOCUMENTS

| | | |
|---|---|---|
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

SYSTEM OF MEDICAL DEVICES AND METHOD FOR PERICARDIAL PUNCTURE

FIELD

This document relates to medical devices. More specifically, this document relates to medical devices that can be used in pericardial puncture, and related methods.

SUMMARY

The following summary is intended to introduce the reader to various aspects of the detailed description, but not to define or delimit any invention.

Systems of medical devices are disclosed. According to some aspects a system of medical devices includes a needle extending between a needle proximal portion and a needle distal portion having a puncturing tip, an endoscope extending between an endoscope proximal portion and an endoscope distal portion having a camera, and an introducer for guiding the needle and the endoscope towards a target location. The introducer extends between an introducer proximal portion and an introducer distal portion and has a first lumen extending therethrough from the introducer proximal portion to the introducer distal portion and a second lumen extending therethrough from the introducer proximal portion to the introducer distal portion. The needle is advanceable through the first lumen to position the puncturing tip proud of the introducer distal portion and the endoscope is advanceable through the second lumen to position the camera proximate the introducer distal portion and outside of the second lumen.

In some examples, the introducer extends along a longitudinal axis, the first lumen is centered on the longitudinal axis, and the second lumen is radially offset from the longitudinal axis.

In some examples, the introducer includes a metallic tube and a polymeric sheathing encasing the tube, and the second lumen extends through the polymeric sheathing.

In some examples, the second lumen extends to a distal opening is in a side surface of the introducer.

In some examples, the needle is a radiofrequency needle and the puncturing tip includes a radiofrequency electrode.

In some examples, the needle includes a metallic core and an electrically insulative coating on the metallic core.

In some examples, the needle is a mechanical needle and the puncturing tip includes a sharp tip.

In some examples, the introducer distal portion further includes a radiopaque marker.

In some examples, the introducer has a length of greater than or equal to 5 inches.

In some examples, the introducer has an atraumatic tip.

Methods for pericardial puncture are also disclosed. According to some aspects, a method for pericardial puncture includes: a. percutaneously advancing an introducer towards a pericardium; b. advancing a needle towards the pericardium via the introducer; c. using a camera to assess a position of a distal portion of the introducer and/or a puncturing tip of the needle; and d. puncturing the pericardium with the puncturing tip.

In some examples the method further includes, prior to step c., advancing an endoscope through the introducer towards the pericardium, wherein the endoscope includes the camera.

In some examples, advancing the needle through the introducer includes advancing the needle through a first lumen of the introducer, and advancing the endoscope through the introducer includes advancing the endoscope through a second lumen of the introducer.

In some examples, advancing the needle through the introducer includes advancing the needle along a longitudinal axis of the introducer, and advancing the endoscope through the introducer includes advancing the endoscope along a path that is radially offset from the longitudinal axis of the introducer.

In some examples, the method further includes advancing the camera out of the second lumen via a distal opening in a side surface of the introducer.

In some examples, step d. includes delivering radiofrequency energy to puncture the pericardium.

In some examples, step d. includes mechanically puncturing the pericardium.

In some examples, in step c., the camera is fixed to the introducer.

In some examples, step c. is carried out before step b. and includes assessing the position of the distal portion of the introducer.

In some examples, the method further includes using fluoroscopy to assess the position of the distal portion of the introducer.

BRIEF DESCRIPTION OF THE DRAWINGS

The accompanying drawings are for illustrating examples of articles, methods, and apparatuses of the present disclosure and are not intended to be limiting. In the drawings.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein is a system of medical devices that includes a needle, an endoscope, and an introducer. The system of medical devices can be used in pericardial puncture procedures, in which the pericardium is punctured to gain access to the epicardium or pericardial space. In such procedures, the introducer can be percutaneously advanced towards the heart, preferably with the needle and the endoscope received in the introducer during advancement of the introducer. The endoscope can then be used to assess the position of the introducer and/or the needle with respect to the target tissue, for example to confirm that the introducer is in the desired position for pericardial puncture with the needle. Once the position of the introducer and/or the needle has been assessed with the endoscope, the needle can be used to puncture the pericardium. By providing an endoscope as part of the system, patient safety can be enhanced.

Figure 1:
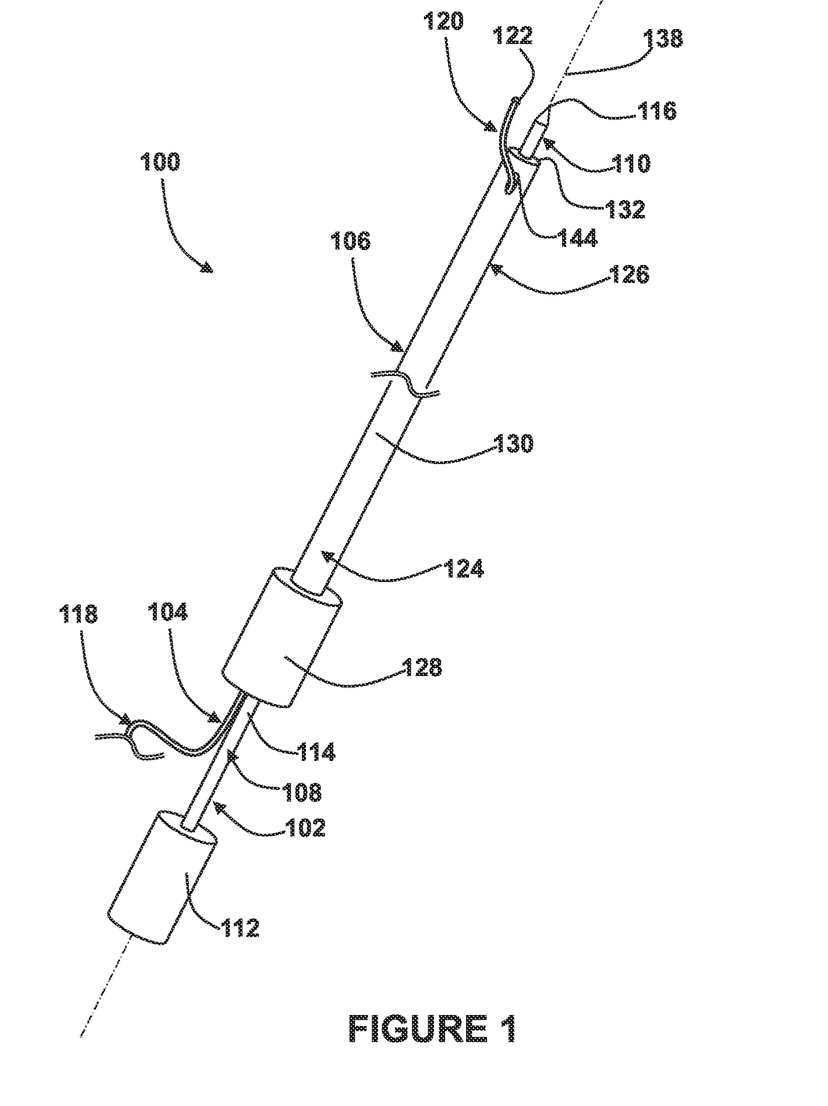
FIG. 1 is a perspective view of a system of medical devices, in an assembled state.

Referring now to FIG. 1, an example system 100 of medical devices is shown. The system 100 generally includes a needle 102, an endoscope 104, and an introducer 106. The introducer 106 can serve to guide both the needle 102 and the endoscope 104 towards a target location in a patient's body (e.g. the heart). The endoscope 104 can be used to assess the position of the introducer 106 and/or the needle 102, and the needle 102 can be used to puncture the target location.

Figure 2:
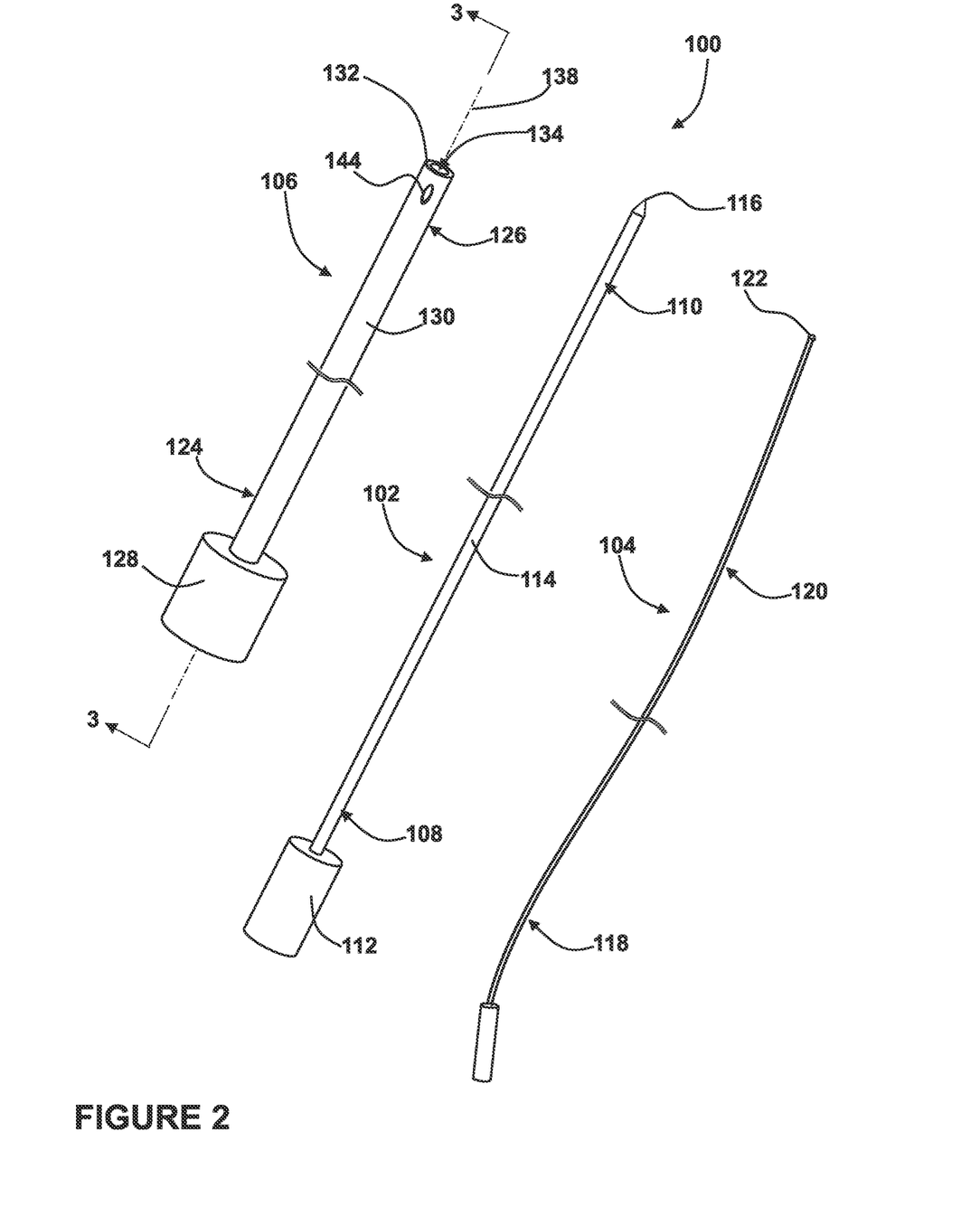
FIG. 2 is a perspective view of the system of medical devices of FIG. 1, in an unassembled state.

Referring to FIG. 2, the needle 102 is elongate and extends between a proximal portion 108 (also referred to herein as a "needle proximal portion"), which can be grasped and/or manipulated by a user, and a distal portion 110 (also referred to herein as a "needle distal portion"), which can be guided towards a target location in a patient's body. The needle 102 includes a hub 112 at the proximal portion 108, and a shaft 114 that extends from the hub 112. The distal portion 110 incudes a puncturing tip 116. In the example shown, the needle 102 is a mechanical needle, and the puncturing tip 116 is in the form of a sharpened end of the shaft 114. For example, the puncturing tip 116 can be beveled or pyramidal or conical (as shown).

In alternative examples, the needle can be a radiofrequency needle. In such examples, the shaft can include an electrically conductive core and an electrically insulative coating on the core, and the puncturing tip can include a radiofrequency electrode, which can be in the form of an electrically exposed tip of the core. Furthermore, in such examples, the system can include a radio frequency generator, for delivery radiofrequency energy to the needle.

The needle 102 can optionally include one or more radiopaque markers in the distal portion 110, such as a platinum or iridium band or coating (not shown), to facilitate viewing of the needle 102 under fluoroscopy.

Referring still to FIG. 2, the endoscope 104 can be a commercially available or publicly known endoscope, and is not described in detail herein. Briefly, in the example shown, the endoscope 104 extends between a proximal portion 118 (also referred to herein as an "endoscope proximal portion") and a distal portion 120 (also referred to herein as an "endoscope distal portion"). The distal portion 120 includes a camera 122 for obtaining images (i.e. still images or video recordings) of the region adjacent the distal portion 120, and the proximal portion 118 can be connected to an imaging system (not shown), which can include a display for displaying the images obtained by the camera 122. The camera can be of various configurations, and can include, for example, optical fibers and lenses. The endoscope 104 can be generally flexible and steerable, in order to direct the camera 122 to a desired location and/or position within a patient's body. The camera 122 can be right at the distal tip and distally facing (as shown), or can be on a side surface of the endoscope.

Figure 3:
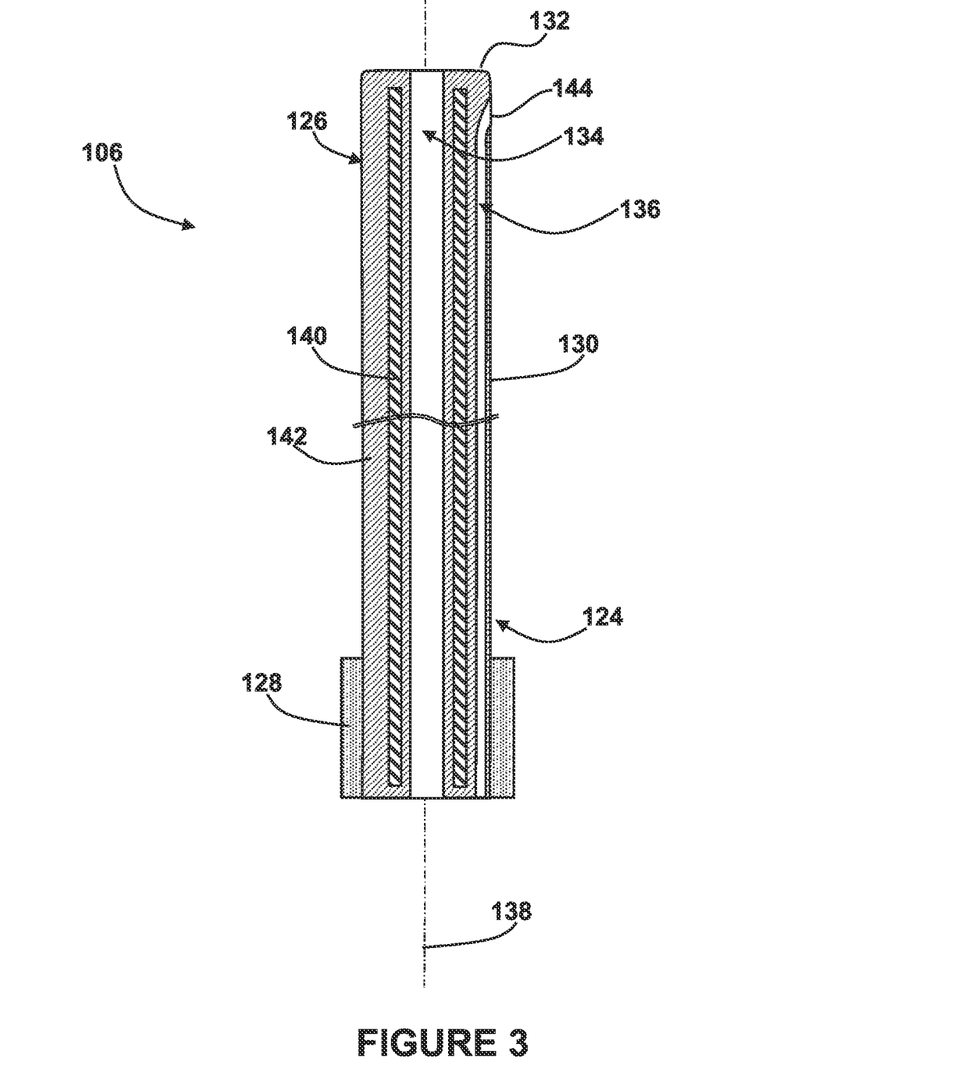
FIG. 3 is a cross-section taken along line 3-3 in FIG. 2.

Referring still to FIG. 2 and also to FIG. 3, in the example shown, the introducer 106 extends between a proximal portion 124 (also referred to herein as an "introducer proximal portion"), which can be grasped and/or manipulated by a user, and a distal portion 126 (also referred to herein as an "introducer distal portion"), which can be guided towards a target location in a patient's body. The introducer 106 includes a hub 128 at the proximal portion 124, and a shaft 130 that extends from the hub 128. The distal portion 126 terminates in a distal tip 132, which is atraumatic.

Figure 4:
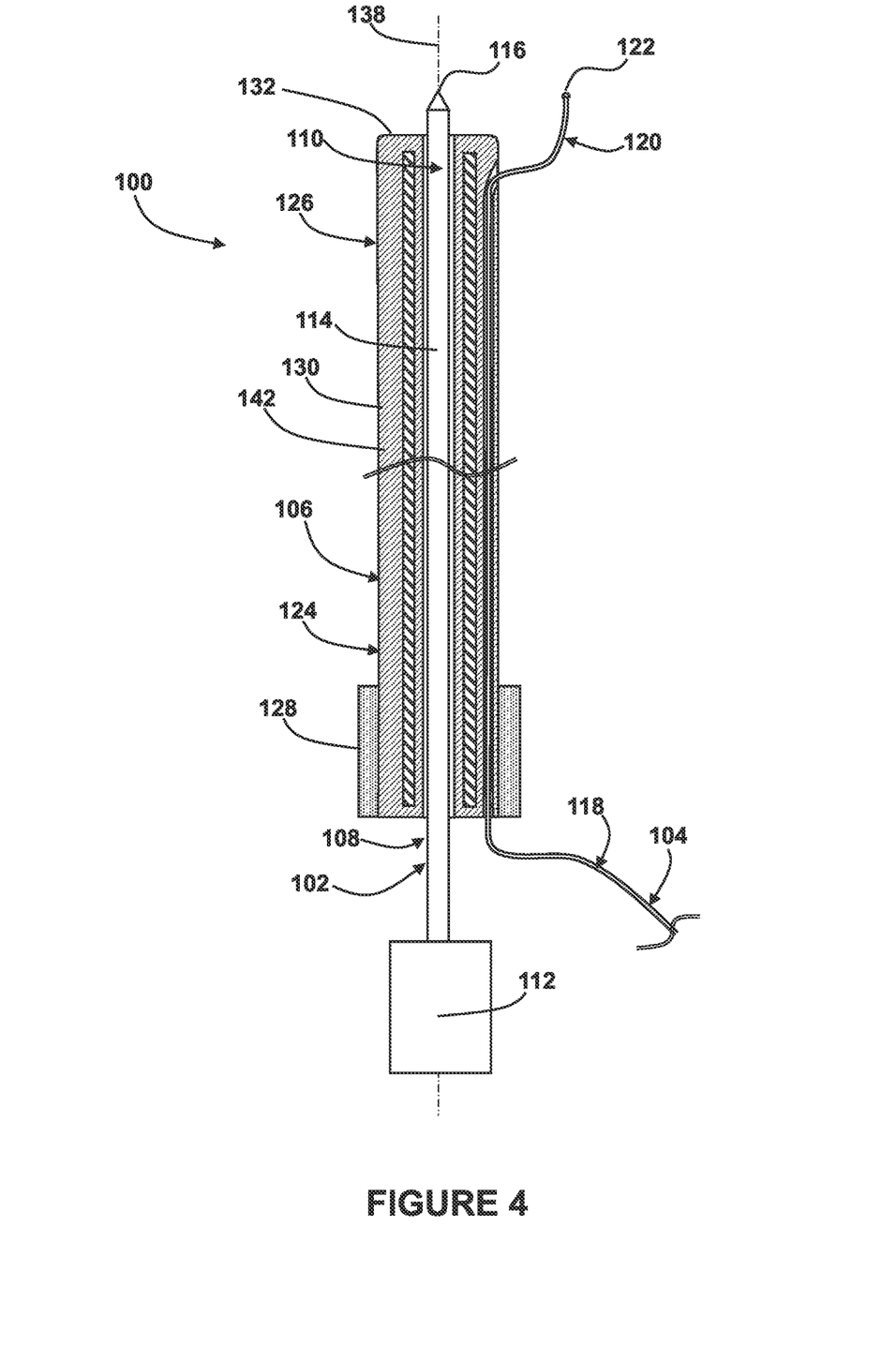
FIG. 4 is a cutaway view of the system of medical devices of FIG. 2.

Referring to FIG. 3, in the example shown, the introducer 106 has a first lumen 134 extending therethrough, from the introducer proximal portion 124 to the introducer distal portion 126, and a second lumen 136 extending therethrough from the introducer proximal portion 124 to the introducer distal portion 126. Referring to FIG. 4, the needle 102 is advanceable through the first lumen 134 (not labelled in FIG. 4), to position the puncturing tip 116 proud of the introducer distal portion 126, to puncture a target location. The endoscope 104 is advanceable through the second lumen 136 (not labelled in FIG. 4), to position the camera 122 proximate the introducer distal portion 126 and outside of the second lumen 136, to obtain images of the introducer distal portion 126, needle distal portion 110, and/or target location.

Referring still to FIG. 3, in the example shown, the introducer 106 extends along a longitudinal axis 138 between the proximal portion 124 and the distal portion 126. The first lumen 134 is centered on the longitudinal axis 138, while the second lumen 136 is radially offset from the longitudinal axis 138. More specifically, the introducer 106 includes a metallic tube 140 (e.g. a stainless steel hypotube), and a polymeric sheathing 142 (e.g. a lubricious polymeric sheathing such as polytetrafluoroethylene) encasing the tube 140. The first lumen 134 extends longitudinally through the tube 140 and the sheathing 142, while the second lumen 136 is radially outboard of the tube 140 and extends through only the sheathing 142. The second lumen 136 extends to a distal opening 144 that, in the example shown, is in a side surface of the introducer 106. In alternative examples, the distal opening can be at the distal tip 132 of the introducer.

The introducer 106 can have a length of, for example, about 5 inches or more, in order to percutaneously reach the pericardium. The needle 102 and endoscope 104 can have a length that is greater than that of the introducer.

The introducer 106 can optionally include one or more radiopaque markers in the distal portion 126, such as a platinum or iridium band (not shown) embedded in the polymeric sheathing 142 or a radiopaque filler in the polymeric sheathing 142, to facilitate viewing of the introducer 106 under fluoroscopy.

In use, the introducer 106 can be percutaneously advanced towards a target location in a patient's body (e.g. towards the pericardium via the subxiphoid approach). Preferably, the endoscope 104 and needle 102 are advanced together with the introducer 106, so that the needle facilitates piercing of adipose tissue etc. (however, the needle 102 and endoscope 104 may be advanced after the introducer, either concurrently, or in sequence by first advancing the needle 102 and then the endoscope 104, or vice versa). The needle 102 can be advanced via the first lumen 134 (i.e. along the longitudinal axis 138 of the introducer 106), and the endoscope 104 can be advanced via the second lumen 136 (i.e. along a path that is radially offset from the longitudinal axis 138 of the introducer 106). Preferably, the needle 102 is advanced together with the introducer 106 with the puncturing tip 116 proud of the introducer until the introducer 106 and needle 102 are proximate the pericardium, and then the needle 102 is retracted slightly, so that the puncturing tip 116 is shy of or flush with the introducer distal tip 132, and so that the atraumatic distal tip 132 of the introducer first contacts the pericardium. The atraumatic distal tip 132 can allow the introducer 106 to safely dock with the target tissue before puncturing, and can prevent premature puncturing. Optionally, fluoroscopy can be used to confirm the position of the introducer 106 and the needle 102.

Once the distal tip 132 contacts the pericardium, the endoscope 104 can be advanced out of the second lumen 136 via the distal opening 144, to position the endoscope 104 such that the distal portion 126 of introducer 106 and/or the target location can be captured with the camera 122. The camera 122 can then be used to assess the position of the distal portion 126 of the introducer 106. Optionally, a fluid can be flushed through the distal opening, to provide a clear view for the camera 122.

If it is determined with the use of the endoscope 104 that the distal portion 126 of the introducer 106 is in the desired position (e.g. in contact with the pericardium at a desired location for puncture), the needle 102 can then be advanced out of the introducer 106, in order to puncture the pericardium with the puncturing tip 116. In the example shown, the needle 102 can mechanically puncture the pericardium; in alternative examples, the needle can deliver radiofrequency energy to puncture the pericardium.

Alternatively, if it is determined with the use of the endoscope 104 that the distal portion 126 of the introducer 106 is not the desired position (e.g. if the distal portion 126 is not in contact with the pericardium at a desired location for puncture), the introducer 106 can be repositioned, and the camera 122 can again be used to assess the position of the distal portion 126 of the introducer 106. When it is determined with the use of the endoscope 104 that the distal portion 110 of the introducer 106 is in the desired position (e.g. in contact with the pericardium at a desired location for puncture), the needle 102 can then be advanced out of the introducer 106, in order to puncture the pericardium with the puncturing tip 116.

Optionally, after the puncturing tip 116 has been advanced out of the introducer 106, the camera 122 can be used to assess the position of the puncturing tip 116.

After the pericardium has been punctured, a subsequent medical procedure can be carried out—e.g. the needle 102 can be withdrawn through the introducer and a guidewire can be advanced through the introducer into the pericardial space.

In alternative examples, rather than using an endoscope that is separate from the introducer, the endoscope can be built into the introducer. That is, a camera can be fixed to the introducer.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A system of medical devices for pericardial puncture, comprising:
    a needle extending between a needle proximal portion and a needle distal portion having a puncturing tip;
    an endoscope extending between an endoscope proximal portion and an endoscope distal portion having a camera; and
    an introducer for guiding the needle and the endoscope towards a target location, the introducer extending between an introducer proximal portion and an introducer distal portion and having a first lumen extending therethrough from the introducer proximal portion to the introducer distal portion and a second lumen extending therethrough from the introducer proximal portion to the introducer distal portion;
    wherein the needle is advanceable through the first lumen to position the puncturing tip proud of the introducer distal portion and the endoscope is advanceable through the second lumen to position the camera proximate the introducer distal portion and outside of the second lumen; and
    wherein the second lumen extends to a distal opening in a side surface of the introducer or in a distal tip of the introducer.

2. The system of claim 1, wherein:
    the introducer extends along a longitudinal axis,
    the first lumen is centered on the longitudinal axis, and
    the second lumen is radially offset from the longitudinal axis.

3. The system of claim 1, wherein:
    the introducer comprises a metallic tube and a polymeric sheathing encasing the tube, and
    the second lumen extends through the polymeric sheathing.

4. The system of claim 1, wherein the needle is a radiofrequency needle and the puncturing tip comprises a radiofrequency electrode.

5. The system of claim 4, wherein the needle comprises a metallic core and an electrically insulative coating on the metallic core.

6. The system of claim 1, wherein the needle is a mechanical needle and the puncturing tip comprises a sharp tip.

7. The system of claim 1, wherein the introducer distal portion further comprises a radiopaque marker.

8. The system of claim 1, wherein the introducer has a length of greater than or equal to 5 inches.

9. The system of claim 1, wherein the introducer has an atraumatic tip.

10. A system of medical devices for pericardial puncture, comprising:
    a needle extending between a needle proximal portion and a needle distal portion having a puncturing tip;
    an endoscope extending between an endoscope proximal portion and an endoscope distal portion having a camera; and
    an introducer for guiding the needle and the endoscope towards a target location, the introducer extending between an introducer proximal portion and an introducer distal portion and having a first lumen extending therethrough from the introducer proximal portion to the introducer distal portion and a second lumen extending therethrough from the introducer proximal portion to the introducer distal portion;
    wherein the needle is advanceable through the first lumen to position the puncturing tip proud of the introducer distal portion and the endoscope is advanceable through the second lumen to position the camera proximate the introducer distal portion and outside of the second lumen;

wherein the needle is a radiofrequency needle and the puncturing tip comprises a radiofrequency electrode, and wherein the second lumen extends to a distal opening in a side surface of the introducer.

11. The system of claim 10, wherein:
the introducer extends along a longitudinal axis,
the first lumen is centered on the longitudinal axis, and
the second lumen is radially offset from the longitudinal axis.

12. The system of claim 10, wherein:
the introducer comprises a metallic tube and a polymeric sheathing encasing the tube, and the second lumen extends through the polymeric sheathing.

13. The system of claim 10, wherein the second lumen extends to a distal opening in a distal tip of the introducer.

14. The system of claim 10, wherein the needle comprises a metallic core and an electrically insulative coating on the metallic core.

15. The system of claim 10, wherein the introducer distal portion further comprises a radiopaque marker.

16. The system of claim 10, wherein the introducer has a length of greater than or equal to 5 inches.

17. The system of claim 10, wherein the introducer has an atraumatic tip.

* * * * *